(12) United States Patent
Sabogal (10) Patent No.: US 9,096,366 B2
(45) Date of Patent: Aug. 4, 2015

(54) APPARATUS AND METHOD FOR THE CONSERVATION, SHIPMENT AND EXHIBITION OF FRESH FLOWERS

(71) Applicant: Daniel Sabogal, Miami, FL (US)

(72) Inventor: Daniel Sabogal, Miami, FL (US)

( * ) Notice: Subject to any disclaimer, the term of this patent is extended or adjusted under 35 U.S.C. 154(b) by 0 days.

(21) Appl. No.: 14/081,742

(22) Filed: Nov. 15, 2013

(65) Prior Publication Data

US 2015/0136627 A1 May 21, 2015

(51) Int. Cl.

| | | |
|---|---|---|
| B65D 81/02 | (2006.01) | |
| A01G 9/02 | (2006.01) | |
| B65D 81/22 | (2006.01) | |
| A01N 3/00 | (2006.01) | |
| A47G 7/06 | (2006.01) | |
| B65D 25/54 | (2006.01) | |
| B65D 25/20 | (2006.01) | |
| B65D 81/24 | (2006.01) | |
| B65D 85/50 | (2006.01) | |

(52) U.S. Cl.
CPC *B65D 81/22* (2013.01); *A01N 3/00* (2013.01); *A47G 7/06* (2013.01); *B65D 25/205* (2013.01); *B65D 25/54* (2013.01); *B65D 81/24* (2013.01); *B65D 85/505* (2013.01)

(58) Field of Classification Search
USPC ............ 206/204, 423, 488, 775, 779; 53/492, 53/381.1; 47/84
See application file for complete search history.

(56) References Cited

U.S. PATENT DOCUMENTS

| | | | | |
|---|---|---|---|---|
| 2,774,187 A | * | 12/1956 | Smithers | 47/41.12 |
| 4,113,094 A | * | 9/1978 | Collin | 206/423 |
| 4,941,572 A | * | 7/1990 | Harris | 206/423 |
| 5,060,799 A | * | 10/1991 | De Pagter | 206/423 |
| 5,379,549 A | * | 1/1995 | Carcich et al. | 47/84 |
| 6,672,002 B1 | * | 1/2004 | Gumpper | 47/41.01 |
| 6,745,514 B1 | * | 6/2004 | Myrland | 47/84 |
| 7,000,347 B2 | * | 2/2006 | Roskin | 47/41.11 |
| 2008/0099356 A1 | * | 5/2008 | Keller et al. | 206/423 |
| 2009/0114560 A1 | * | 5/2009 | Harshman | 206/423 |
| 2012/0048761 A1 | * | 3/2012 | Ginjo | 206/423 |

\* cited by examiner

*Primary Examiner* — Jacob K Ackun (57) ABSTRACT

The present disclosure includes an apparatus and method of use to facilitate storing, conserving and exhibition of fresh flowers particularly where the flowers originate in country such as Columbia and are internationally shipped to a country such as the United States and doing so while the flowers are maintained completely hydrated. Hydration is accomplished by placing fresh flowers stems into florists' foam which is soaked to make hydration continuously available to the fresh flowers during storage shipment and exhibition. Thus there is no water to leak from the packaging and no need to maintain the shipping container in a vertical upright position. The packaging further includes perforations so the fresh flowers can breath while being stored and in transit and the packaging includes a stand for exhibition of the flowers at a convenient and attractive height of about waist high when the fresh flowers arrive at a retailer having no special equipment or personnel for the care of perishables. The exhibition box contained within the shipping container is equipped with a custom symmetric geometric shaped opening for firm support of the bucket containing the fresh flowers and soaked florists' foam. The disclosure further includes a series of steps for opening the shipping container, discarding packaging material and placing the bucket of fresh flowers into the top of the exhibition box. Finally, the method includes the optional step of adding water to the bucket.

12 Claims, 6 Drawing Sheets

APPARATUS AND METHOD FOR THE CONSERVATION, SHIPMENT AND EXHIBITION OF FRESH FLOWERS

BACKGROUND OF THE INVENTION

1. Field of the Invention

The present invention relates generally to the field of packaging for shipment, conservation and point of sale display of fresh flowers in a retail facility having no equipment or personnel to care for the flowers until they are sold. It includes special apparatus for the conservation of fresh flower during shipment by keeping them hydrated. But hydration cannot be done with just water in a container because such a configuration is very prone to leakage. That is because the realities of courier shipment are that the shipping containers are not maintained in an upright position. Hydration is maintained by soaking a florist's foam with water and inserting the cut flower stems therein. The foam retains the water but at the same time makes it accessible to the cut flower stems regardless of the orientation of the shipping container.

2. Description of the Prior Art

The present invention relates packaging used for the international shipment of fresh cut flowers within the flower industry, especially during the post harvest stages of storage, conservation, shipment and exhibition of fresh flowers to the public. In the prior art commercial fresh flowers have been packaged from their harvest until their display in commercial points of sale in a manner that causes rapid deterioration such that their vase lives are substantially diminished.

When fresh flowers are shipped from their country of origin, such as Colombia, to both the main cities and remote towns of another country, such as the United States, the conditions of storage, conservation and shipping are even more demanding than when shipment is to a central flower market, or wholesaler. In the former situation, the conditions of storage, conservation and shipment must be all the more carefully planned and controlled to achieve success in the acceptance of these flowers by the trade, and the final consumer. Furthermore, if the fresh flowers are delivered to point of sale retailers who employ people inexperienced in the care and display of fresh flowers, is an additional problem, which can lead to further deterioration of their state.

In the prior art, there has been certain packages for fresh flowers, which allow for their conservation and transport within the same country. In the United States, for example, there are packages that include water buckets, which are transported in refrigerated trucks. Fresh flowers in buckets of water are deemed to be perishables. However, it is not practical to use the above mentioned method when the flowers are being shipped internationally such as from Colombia to the United States, due to the difficulty of transporting products containing water (high shipping costs to attempt to maintain the shipping containers in an upright posit a d restrictions from the shippers to transport water).

As an illustration, of the foregoing, one of the prior art methods of shipment is in packages made up of a plastic container, a cardboard caller and a lid with many openings. The method uses water in the container requiring upright shipping, and requires ground transportation in refrigerated trucks and handling for perishables. Thus it is only applicable for wholesalers and retailers with a perishables distribution center. See www.primrose-flowers.com/pt_procona.html. It is thus way more expensive than the present invention and has much more limited use.

Additionally, there are a great number of potential points of sale that cannot be served because they either are not equipped to handle perishables, or the costs associated with such shipping makes such sales not financially viable.

In the prior art, fresh flowers shipped internationally are usually shipped dry, because, as explained above, shipping in containers of water is not practical. Therefore, when flowers ship from Columbia to the United States arrive in the United States they must either be immediately placed in buckets of water and treated as perishables, or they must be quickly delivered to consumers dry. The cut flowers placed in water are then delivered in refrigerated trucks in water and treated as perishables to such retailers as florists or some larger retail outlets such as Walmart, where there are personnel equipped to handle perishables. However, not all Walmart location are so equipped.

When flowers shipped internationally arrive in the United States they can be delivered to central flower markets or to some retailers like some locations of Walmart where they can be immediately placed in water buckets. They need to unpack, cut the stems, place them in buckets of water and exhibition of them in their shelves, all of which affects the final quality and the final cost of the flowers, not to mention that these packages are trashed and cannot be recycled.

One other option is to hydrate flowers individually by the use of little cups or bags attached to each flower stem separately. This is very expensive and thus not practical for even bouquets of flowers.

SUMMARY OF THE INVENTION

Bearing in mind the foregoing, it is a principal object of the present invention to provide a package for the storage, conservation, shipping and final exhibition of fresh flowers which provides advantages that no other prior art package achieves in its entirety, especially continuous hydration.

Another principal object of the present invention is to provide a package that maintains the same hydration levels of the flowers similar to containers with water which allows for freshness conservation during the packaging process at the post harvesting sites in the originating country all the way through exhibition at the point of sale in the final destination country after international shipping.

A further object of the invention is that continuous hydration allows for addition to the water of nutrients and preservatives now in existence or hereafter developed. So, for example, a floral preservative such as a vasodilator can be added to the water with which the flowers are continuously hydrated.

Another object of the present invention is to provide a package that allows for greater distribution coverage including access to all points of sale that cannot be served regularly by the prior art delivery method of refrigerated trucks because these additional locations are not equipped to handle perishables.

An additional object of the present invention is to provide a package in which fresh flowers remain static but hydrated, which prevents their deterioration due to movement or turns during shipment. Orientation of the package becomes irrelevant with this package, making courier shipment possible with continuously hydrated fresh flowers.

A further object of the present invention is to provide a package in which fresh flowers are kept properly ventilated and hydrated at all times from the time of packaging in the country of origin through international shipping to the point of unpacking and exhibition in the destination country.

An additional object of the present invention is to provide a package that includes one box inside of another box which reinforces the protection of the fresh flowers during shipment.

A further object of the present invention is that the inventive package minimizes handling of the fresh flowers from the moment that they are packaged in the country of origin until sale to the final consumer at the point of sale in the destination country.

Another object of the present invention is that part of the package, specifically the inside box, serves as a stand to facilitate exhibition of the flowers to the public at the point of sale.

A further of the present invention is that the packaging method provide for less waste and flower debris due to the use of the packaging as a stand and the minimal disturbance that the flowers must endure at the hands of a shop keeper without perishability expertise.

One more object of the present invention is that it allows for a prolonged life span of the fresh flowers due to the optimization of the distribution time compared with prior art logistics.

Other Objects and advantages of the present invention will be apparent to those skilled in the art upon reference to the following descriptions and the appended drawings.

In accordance with a primary aspect of the present invention there is provided an apparatus to facilitate storage, conservation and exhibition of fresh flowers particularly where the flowers originate in a country such as Columbia and are internationally shipped to a country such as the United States and doing so while the flowers are continuously and completely hydrated. Hydration is accomplished by placing fresh flowers stems into florists' foam which is soaked to make hydration continuously available to the fresh flowers during storage, shipment and exhibition. Nutrients and/or preservatives can be added to the water for continuous exposure to the flowers during storage, shipment and exhibition to the potential purchasers.

Thus there is no water to leak from the packaging and no need to maintain the shipping container in a vertical upright position, making courier shipment viable for the first time with hydrated fresh flowers. The packaging further includes perforations so the fresh flowers can breath while being stored and in transit and the packaging includes a stand for exhibition of the flowers at a convenient and attractive height of about waist high when the fresh flowers arrive at a retailer having no special equipment or personnel for the care of perishables. The exhibition box contained within the shipping container is equipped with a custom symmetric geometric shaped opening for firm support of the bucket containing the fresh flowers and soaked florist' foam.

In accordance with a secondary aspect of the present invention, there is provides a method of use of the apparatus of the present invention. The method comprises a series of steps for opening the shipping container, discarding packaging material, inverting the exhibition box which is shipped upside down in the outside container box, and placing the bucket of fresh flowers into a special opening in the top of the exhibition box for secure exhibition of the fresh flowers to potential purchasers. The method finally contains an optional step of adding water to the bucket to compensate for water consumption during shipment.

In accordance with a tertiary aspect of the invention there are provided packaging materials such as the cardboard boxes, wooden protective sticks, plastic bag, and plastic buckets that are either inherently biodegradable such as the cardboard and wooden sticks, or are those that are formulated from biodegradable plastic such as the plastic bags and buckets. Biodegradability of plastic is accomplished by the inclusion of additives to the plastic resin when plastic articles are being formed.

BRIEF DESCRIPTION OF THE DRAWINGS

Various other features of the invention will become apparent to those skilled in the art from the following, discussion taken in conjunction with the appended drawings in which.

DETAILED DESCRIPTION OF THE PREFERRED EMBODIMENT

As required, a detailed embodiment of the present invention is disclosed herein; however, it is to be understood that the disclosed embodiment is merely exemplary of the invention which may be embodied in various other forms. Therefore, specific structural and functional details disclosed herein are not to be interpreted as limited, but merely as a basis for the claims and as representative basis for teaching one skilled in the art to variously employ the present invention in virtually any appropriately detailed structure.

Reference now made to the drawings, wherein like characteristics and features of the present invention shown in the various figures are designated by same reference numerals.

Figure 1:
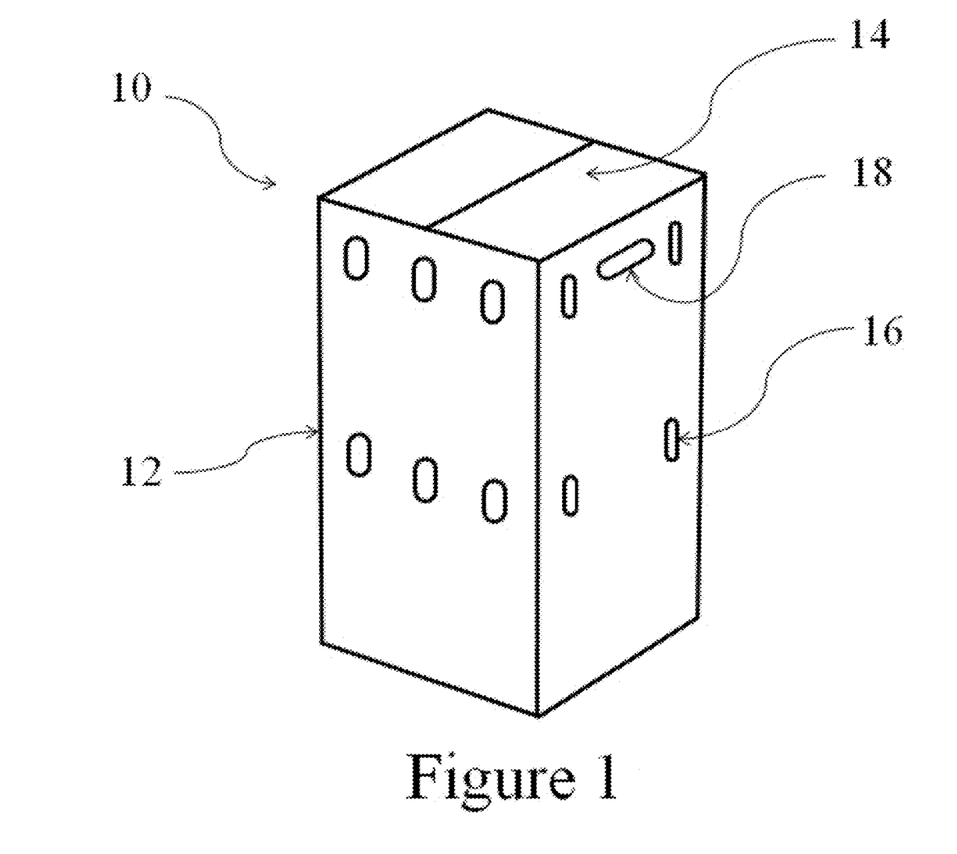
FIG. 1 is a perspective view drawing of the exterior of the shipping container of the present invention.

FIG. 1 is a perspective view of the present invention 10 including particularly the shipping container 12 which is an external box, preferably made of corrugated cardboard, with a closed base (not visible), built in a rectangular parallelogram shape, where the exterior box 12 shows upper hinged lids 14 for closing the shipping container, flattened oval perforations 16 in all of the lateral walls of the shipping container 12 as well as a handle opening 18. A second handle opening that is a mirror image of handle opening 16 on the back of the box is not visible.

Figure 2:
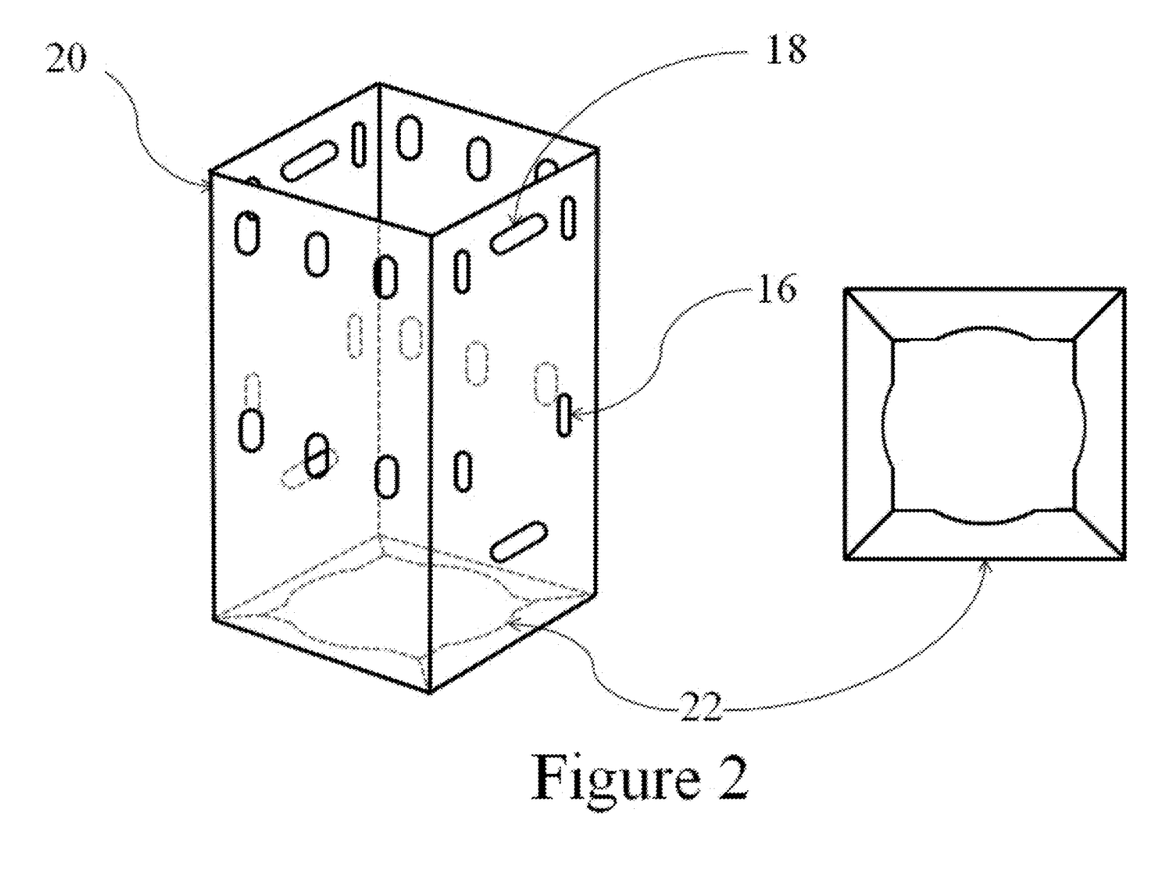
FIG. 2 is a combination perspective view showing the exterior of an interior box that is contained within the container of FIG. 1, referred to hereinafter as the exhibition box, which also shows a top view of the inverted exhibition box which includes a specially shaped opening for secure support of the bucket of fresh flowers.

FIG. 2 shows an interior box termed an exhibition box 20 which also contains handle perforations 18 that are co-linear to the handle perforations 18 in the exterior box 12 and also flattened oval perforations 16 that are co-linear with the flattened oval perforations 16 of exterior box 12. The flattened oval perforations 16 in FIGS. 1 and 2 in all lateral walls thereof facilitate breathing and aeration of the fresh flowers.

The exhibition box 20 of FIG. 2 is placed inside external box 12 as shown in FIG. 2, but is must be inverted when removed from external box 12 for its display function as will hereinafter be described.

Figure 3:
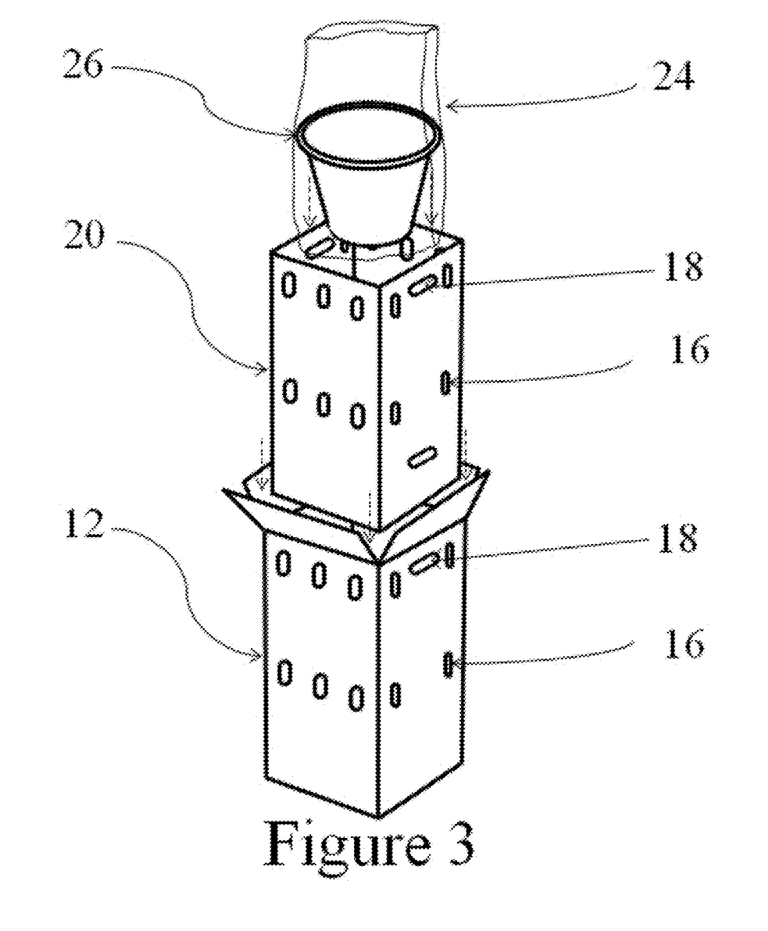
FIG. 3 is a exploded view of the primary contents of the shipping container of FIG. 1 showing the container of FIG. 1 opened, the exhibition box removed therefrom and disposed directly above the opened container of FIG. 1, above which is the bucket and a plastic bag.

Exhibition box 20 has a semi-open top 22 which includes an opening having a custom symmetric geometric shape. The top 22 can be described as a square circumscribed by another square that is the external dimensions of the exhibition box 20. The inner square has its perimeter modified by portions shaped as outwardly bending arches. Note once again that exhibition box 20 is placed upside down in exterior box 12 such that the flattened oval perforations 16 of both boxes are co-linear as are the handle openings 18 in both the interior exhibition box 20 and exterior container 12. This is shown in the exploded view of FIG. 3. The arrangement of the two boxes one inside the other in snug fitting relationship to provide reinforced walls, which offer additional protection for the flowers during their storage and shipment. Also in FIG. 3 can be seen to plastic bag 24 in which is placed bucket 26. Bucket 26 has a greater outside diameter than plastic bag, 24 which facilitates bucket 26 to be tightened to the lateral internal walls of the exhibition box 20. Note further in FIG. 3 that the plastic bag 24, which includes bucket 26 are inserted to the bottom of the assembly of the two boxes inside, of each other and plastic bag 24 is kept open during shipment to ensure breathing and aeration of the fresh flowers as described in subsequent drawings.

Figure 4:
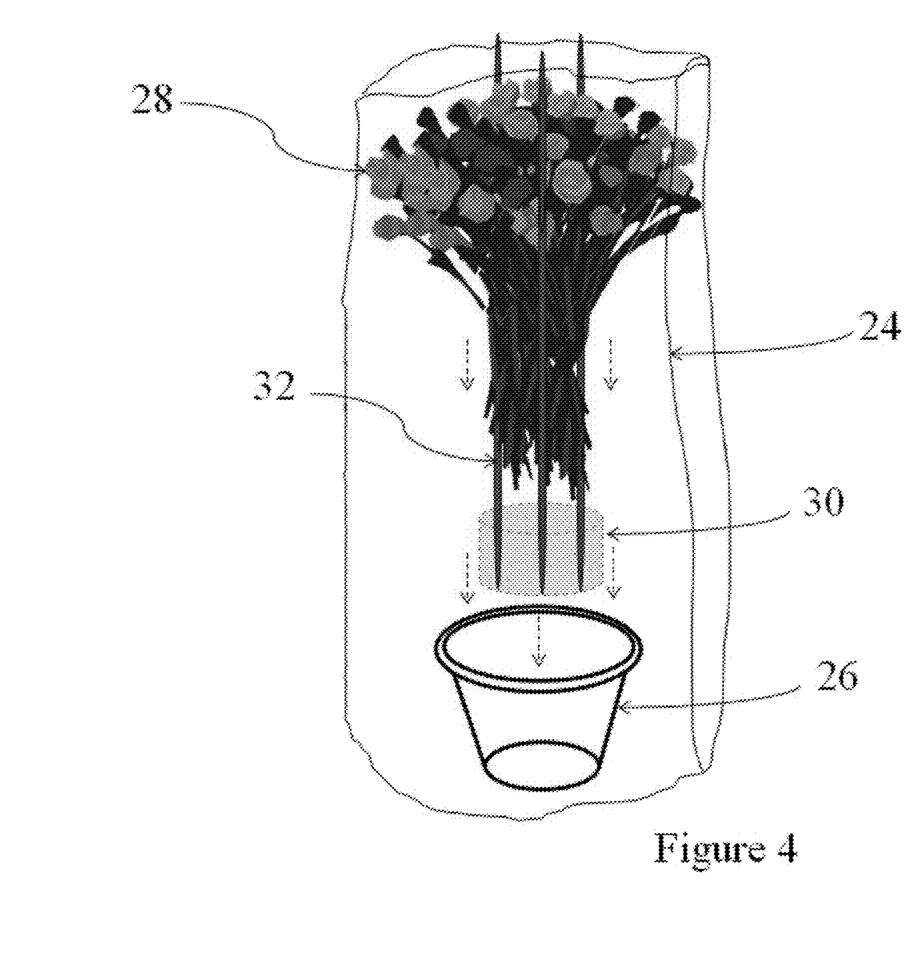
FIG. 4 is an exploded view of some of the contents of the shipping container including, first, the plastic bag within which is contained the bucket, a circular block of florists foam which is soaked with water to hydrate the flowers, at least three protective sticks, and the fresh flowers which are preferably formed into one or more bouquets.

In FIG. 4, the stems of flowers 28 are arranged in bucket 26 inside of a circular block of florists' foam 30 which is soaked with water such that all of the water is trapped in the foam 30, but continuously available to the stems of flowers 28. Also contained within plastic bag 24 are a plurality of protective sticks 32, preferably at least 3 in number, that protect flowers 28 from being, crushed in the vertical dimension during the shipment process. The flowers 28 are inserted one by one into the florists' foam 30 so that each flower stem is immersed in the soaked florist foam to maintain hydration throughout the storage and shipping process.

The combination of the open plastic bag 24 bucket 26, florist foam 30, protective sticks 32 and flowers 28 once assembled together are then placed all the way to the bottom of inverted exhibition box 20 and exterior box 12 such that the lids 14 may be closed and sealed for shipment. Note that the protective sticks 32 as seen in FIG. 4 extend for the entire height of external box 12 when the lids 14 are closed. At this point flowers 28 are ready for their preservation, storage and shipment to domestic or international destinations.

Figure 5:
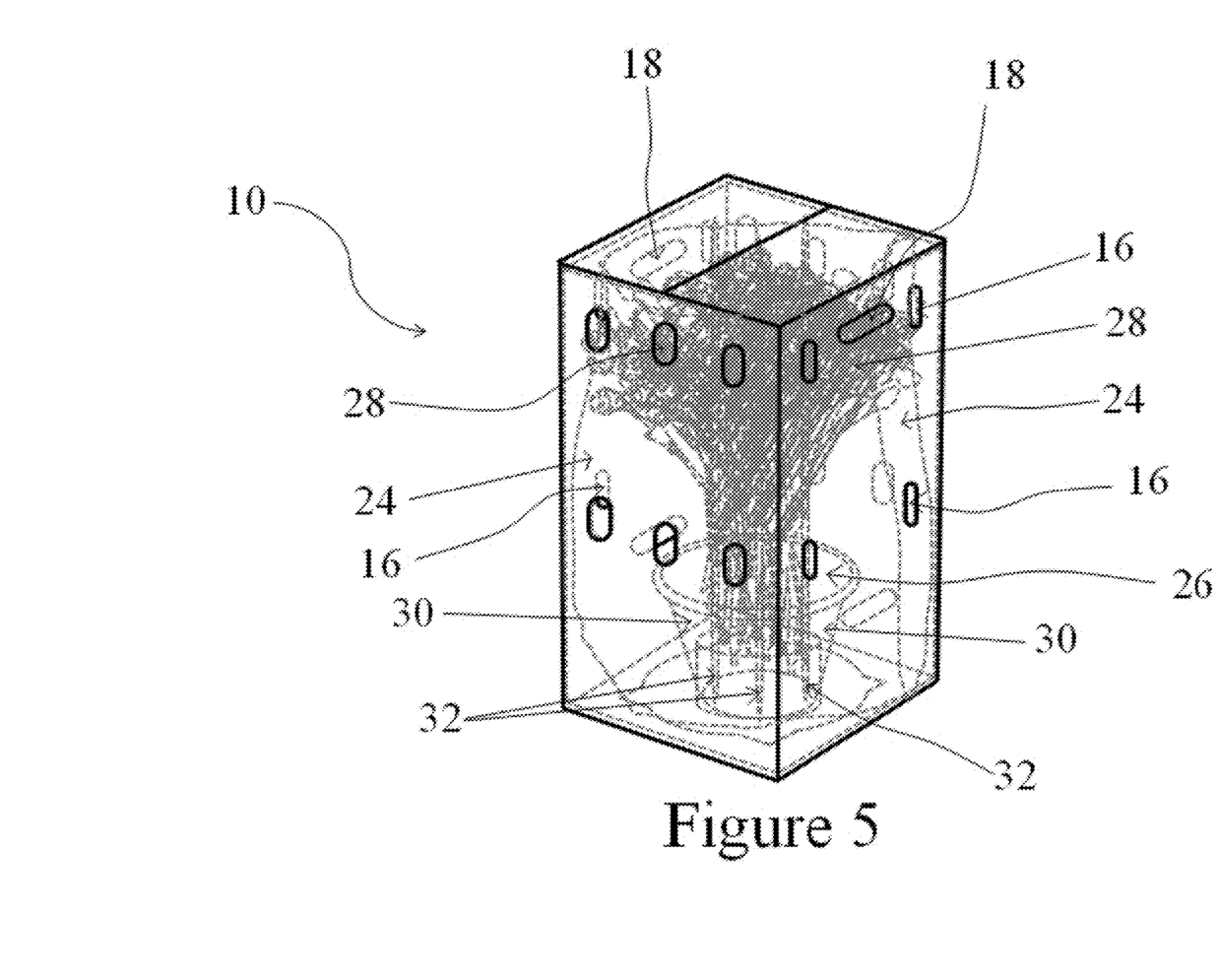
FIG. 5 shows a prospective view of the shipping container of FIG. 1 which is complete with its contents packaged therein and with the contents all shown in phantom.

FIG. 5 shows the contents of the inventive container 10 in phantom when they are all completely assembled. So, in FIG. 5 can be seen plastic bag 24, flowers 28, bucket 26, soaked florists' foam 30 and protective sticks 32. It should be noted that this configuration, especially with the water trapped inside the foam 30, renders the orientation of the closed shipping container 12 irrelevant, such that shipment can be by carriers that make no effort to keep shipped packages upright. Such carriers include couriers such as Federal Express. This reduces shipping, cost as well as providing excellent care of the fresh flowers.

Figure 6:
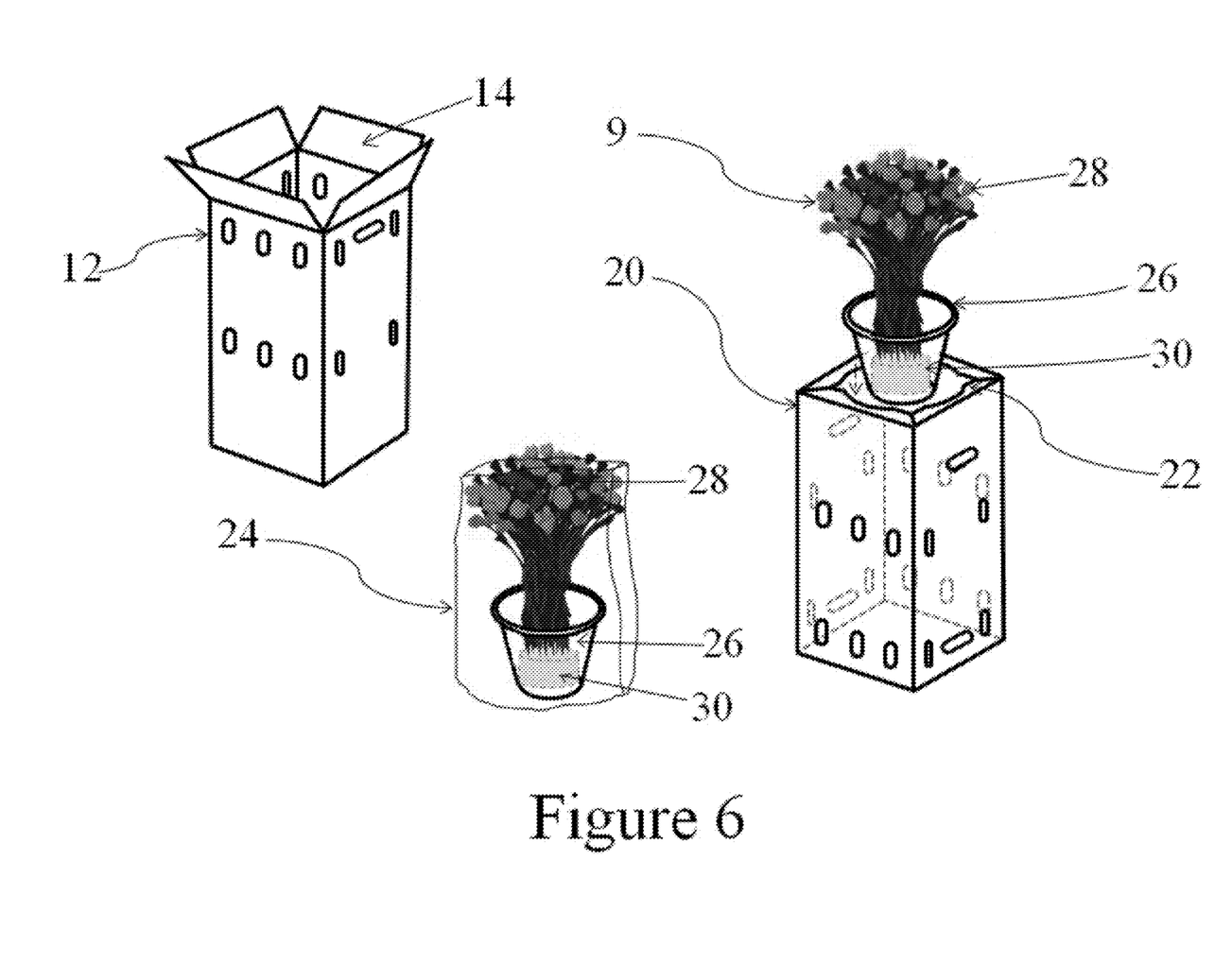
FIG. 6 is a prospective view with sequence drawings showing the opened shipping container of FIG. 1, the flowers in the bucket, both of which are shown in the plastic bag as has been removed from the shipping container of FIG. 1, and then the exhibition box turned right side up for use with the bucket and flowers placed above the opening, in the top of the exhibition box preparatory to display of the flowers.

Turning finally to FIG. 6, external box 12 is opened and plastic bag 24 is removed which contains bucket 26, flowers 28 and soaked florists' foam 30. Exhibition box 20 is also removed from external box 12 and inverted so that the top with the custom symmetric geometric shape 22 is now at the top and is ready to receive bucket 26, with flowers 28 still inserted into soaked florists' foam 30 for exhibition of the product. Thus, the retailer employee who receives the package needs only to open the top lids 14 of the exterior container 12, pull out the bag 24 and take out the contents, namely bucket 26, florists' foam 30 and protective sticks 32 from the plastic bag 24. The plastic bag 24 and protective sticks 32 can be set aside. Then the flowers 28, bucket 26 and florists' foam 30 can be inserted to the semi-open custom symmetric geometric shape 22 of the exhibition box 20. The flowers 28 can be displayed with or without additional hydration such that no skill and experience in the handling of perishables is required.

The semi-open, custom symmetric geometric shaped opening 22 is an essential characteristic of exterior of the exhibition box 20 at the moment of assembling it for the presentation of the flowers because its specific shape allows the insertion of the bucket 26 and the flowers 28 contained in the florists foam 30 such that there is no risk of any of the flowers falling. The exterior of the exhibition box 20 is presented without any damage from shipping and is decorated and ready for exhibition of the flowers 28 to the public. What follows is a description of the method of use of the foregoing apparatus as a portion of the present invention.

The foregoing describes the detailed description of the apparatus of the present invention, while the following is a detailed description of the method of use.

The method commences with receipt of at least one closed container external box 12 having top panels 14 sealed. As shown in FIG. 5, it contains plastic bag 24, flowers 28, bucket 26, soaked florists' foam 30 and protective sticks 32. The closed container 12 is opened and the plastic bag 24 is removed. Then the exhibition box 20 is also removed and turned right side up because it was upside down in the outside box 12. Then the protective sticks 32 are removed from the bucket 26 and finally the flowers 28 in the bucket 26 are removed from the plastic bag 24. At this point one liter of water more or less is preferably added to the bucket 26. Finally, the bucket 26 of fresh flowers 28 is inserted into the custom symmetric geometric shaped opening 22 at the top of the exhibition box 20 for the exhibition of the flowers 28.

While the invention has been described, disclosed, illustrated and shown in various terms or modifications which it has assumed in practice, the scope of the invention is not intended to be, nor should it be deemed to be, limited thereby and such other modifications as be suggested by the teachings herein are practically reserved especially as they fall within the breath and scope of the claims here appended.

What is claimed is:

1. An apparatus for the conservation, shipment and exhibition of fresh flowers comprising;
   a closed external box, having at least one perforation in its lateral walls;
   an interior exhibition box having a semi-open top and at least one perforation in its lateral walls which perforation is at least partially co-linear with the perforation in the external box:
   a bucket which includes a soaked block of foam;
   fresh flowers, the stems of which are stuck into the soaked foam; and
   at least one protective stick placed among the fresh flowers.

2. The apparatus of claim 1 in which the two boxes one inside the other in snug fitting relationship provides reinforced walls, which offer additional protection for the flowers during their storage and shipment.

3. The apparatus of claim 1 which further con rises a hag containing the bucket, fresh flowers and protective stick(s) inserted all the way into the exhibition box.

4. The apparatus of claim 3 in which the at least one perforation in the lateral walls of both the external box and exhibition box are plural in number and have a flattened oval shape.

5. The apparatus of claim 4 in which the bag is left open to allow the fresh flowers to breath through the flattened oval perforations in both the external box and the interior exhibition box that are at least partially co-linear with each other.

6. The apparatus of claim 4 in which the exhibition box has an open base and where the flattened oval shaped perforations its lateral walls are at least partially co-linear with the flattened oval perforations in the external box when the exhibition box is inverted and disposed within the exterior box.

7. The apparatus of claim 6, which further comprises hand hold perforations in both the external box and the inverted exhibition box which perforations are co-linear with each other which facilitates handling of the complete apparatus of claim 5.

8. The apparatus of claim 1, in which the semi-open top of the exhibition box is defined as a square circumscribed by another, where the interior square has its perimeter modified by outwardly bending portions shaped as arches and wherein an opening whose perimeter is defined by the modified interior square is sized to firmly hold the bucket for exhibition of the fresh flowers.

9. The apparatus of claim 1 in which the at least one protective stick is plural in number dispersed among the fresh flowers and are formed with a length that extends from a closed base of the external box to a closed top thereof.

10. The apparatus of claim 1, which further comprises decorative indicia on lateral walls of the exhibition box to enhance its aesthetics when the same is used as a base for exhibition of fresh flowers.

11. A method of use of an apparatus for the conservation, shipment and exhibition of fresh flowers comprising;

receiving delivery of an apparatus that includes a dosed external box, an interior exhibition box with an open base and placed within the closed exterior box, said interior exhibition box having a semi-open top, a bucket which includes a soaked block of foam, fresh flowers, the stems of which are stuck into the soaked foam, and a plurality of protective sticks dispersed among the fresh flowers, and a bag containing the bucket, fresh flowers and protective sticks;

opening closed the external box;

removing, the bucket with fresh flowers, protective sticks and soaked foam by gently pulling the top of the bag upward;

removing the inverted exhibition box from the external box;

removing the bucket containing the florist foam, protective sticks and fresh flowers from the protective bag;

removing the protective sticks from the fresh flowers; and placing the bucket of fresh lowers in the semi-open top of the exhibition box after turning it right side up for exhibition of the fresh flowers.

12. The method of claim 11 which further comprises pouring a modest amount of water inside the bucket.

* * * * *